US005710352A

United States Patent [19]
Tung

[11] Patent Number: 5,710,352
[45] Date of Patent: Jan. 20, 1998

[54] VAPOR PHASE PROCESS FOR MAKING 1,1,1,3,3-PENTAFLUOROPROPANE AND 1-CHLORO-3,3,3-TRIFLUOROPROPENE

[75] Inventor: Hsueh Sung Tung, Erie County, N.Y.

[73] Assignee: AlliedSignal Inc., Morristown, N.J.

[21] Appl. No.: 716,013

[22] Filed: Sep. 19, 1996

[51] Int. Cl.⁶ .................................................. C07C 17/08
[52] U.S. Cl. .................... 570/166; 570/167; 570/168; 570/169
[58] Field of Search .................................. 570/166, 167, 570/168, 169

[56] References Cited

U.S. PATENT DOCUMENTS 5,574,192  11/1996  Van Der Puy et al. ............... 570/168

*Primary Examiner*—Alan Siegel
*Attorney, Agent, or Firm*—Lois A. Gianneschi; Jay P. Friedenson

[57] ABSTRACT

A method for the preparation of 1,1,1,3,3-pentafluoropropane (HFC-245fa) and 1-chloro-3,3,3-trifluoropropene (HCFC-1233). 1,1,1,3,3-pentachloropropane (HCC-240fa) is fluorinated with HF in a vapor phase in the presence of a vapor phase catalyst. The HCFC-1233 and any co-produced 1,3,3,3-tetrafluoropropene (HFC-1234) are recycled for further fluorination by HF for a greater than 99% HCC-240fa conversion.

24 Claims, No Drawings

VAPOR PHASE PROCESS FOR MAKING 1,1,1,3,3-PENTAFLUOROPROPANE AND 1-CHLORO-3,3,3-TRIFLUOROPROPENE

BACKGROUND OF THE INVENTION

1. Field of the Invention

The present invention relates to the preparation of hydrofluorocarbons and hydrochlorofluorocarbons. More particularly, the invention pertains to a method for the manufacture of 1,1,1,3,3-pentafluoropropane (HFC-245fa) and 1-chloro-3,3,3-trifluoropropene (HCFC-1233) by a vapor phase manufacturing process in the presence of a vapor phase catalyst.

2. Description of the Prior Art

In recent years, there has been widespread concern that certain chlorofluorocarbons might be detrimental to the Earth's ozone layer. As a result, there is a worldwide effort to use halocarbons which contain fewer chlorine substituents. The production of hydrofluorocarbons, i.e. compounds containing only carbon, hydrogen and fluorine has thus been the subject of increasing interest to the fluorocarbon industry which has focused its attention on developing environmentally desirable products for use as solvents, foam blowing agents, refrigerants, cleaning agents, aerosol propellants, heat transfer media, dielectrics, fire extinguishing compositions and power cycle working fluids. In this regard, 1,1,1,3,3-pentafluoropropane (HFC-245fa) is a hydrofluorocarbon having zero ozone depletion potential, and is considered a replacement for chlorofluorocarbons in many of the above applications. 1-chloro-3,3,3,-trifluoropropene (HCFC-1233) is another hydrocarbon replacement which is useful as a refrigerant, a foam blowing agent, as well as an intermediate in the production of HFC-245fa and other fluorinated materials.

It is known in the art to produce hydrofluorocarbons (HFCs) by reacting hydrogen fluoride with various hydrochlorocarbon compounds. Such HFCs are not only considered to be much more environmentally advantageous than hydrochlorofluorocarbons (HCFCs) or chlorofluorocarbons (CFCs) because they are non-ozone depleting, but they are also advantageously non-flammable and non-toxic. Although HFC-245fa itself is well known in the art as described in U.S. Pat. No. 2,942,036, Canadian 684,687, EP 381 986A, IP 02,272,086 and WO 95/04022, which are incorporated herein by reference, it has been a problem in the art to conduct an economical process for its continuous preparation.

SUMMARY OF THE INVENTION

We have discovered an efficient, economical means of manufacturing HFC-245fa on a commercial scale via a vapor reaction with hydrogen fluoride. This vapor phase reaction is much less corrosive than a liquid phase reaction. In addition, any unreacted HF and by products produced may also be optionally removed and recycled to produce additional quantities of HFC-245fa.

The invention provides a process for the preparation of 1,1,1,3,3-pentafluoropropane which comprises:

(a) conducting a fluorination reaction by reacting 1,1,1,3,3- pentachloropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and (b) separating 1,1,1,3,3-pentafluoropropane from said reaction product.

The invention also provides a process for the preparation of 1-chloro-3,3,3-trifluoropropene which comprises:

(a) conducting a fluorination reaction by reacting 1,1,1,3,3-pentachloropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and (b) separating 1-chloro-3,3,3-trifluoropropene from said reaction product.

The invention further provides a process for the preparation of 1,1,1,3,3-pentafluoropropane which comprises:

(a) conducting a fluorination reaction by reacting one or more components comprised of 1,1-dichloro-3,3,3-trifluoropropane, 1-chloro-1,3,3,3,-tetrafluoropropane or 1,1,3-trichloro-3,3-difluoropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and (b) separating 1,1,1,3,3-pentafluoropropane from said reaction product.

The invention still further provides a process for the preparation of 1-chloro-3,3,3-trifluoropropene which comprises:

(a) conducting a fluorination reaction by reacting one or more components comprised of 1,1-dichloro-3,3,3-trifluoropropane, 1-chloro-1,3,3,3,-tetrafluoropropane or 1,1,3-trichloro-3,3-difluoropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and (b) separating 1-chloro-3,3,3-trifluoropropene from said reaction product.

DETAILED DESCRIPTION OF THE PREFERRED EMBODIMENT

The 1,1,1,3,3,-pentachloropropane (HCC-240fa) starting material is not generally commercially available, but may be prepared by any means well known in the art. See, for example, B. Boutevin, et al, *Monofunctional Vinyl Chloride Telomers. 1. Synthesis and Characterization of Vinyl Chloride Telomer Standards*, 18 Eur. Polym. J. 675(1982); Chem. Abstr. 97:182966c (1982) and Kotora, et al, *Selective Additions of Polyhalogenated Compounds to Chloro Substituted Ethenes Catalyzed by a Copper Complex;* 44(2) React. Kinet. Catal. Lett. 415 (1991).

Any water in the HF will react with and deactivate the fluorination catalyst. Therefore substantially anhydrous hydrogen fluoride is preferred. By "substantially anhydrous" we mean that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from AlliedSignal Inc. of Morristown, N.J.

Fluorinated catalysts useful in the process of the invention include any catalysts known in the art including, but not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction. The fluorination reaction may be conducted in any suitable fluorination reaction vessel or reactor but it should preferably be constructed from materials which are resistant to the corrosive effects of hydrogen fluoride such as Hastalloy, Inconel, Monel and vessels lined with fluoropolymers.

The reactor is preheated to the fluorination reaction temperature while anhydrous HF is fed to the reactor. The HCC-240fa and HF may be fed to the reactor at any convenient temperature and pressure. In a preferred embodiment either or both of the HCC-240fa and HF are prevaporized or preheated to a temperature of from about 30° C. to about 300° C. prior to entering the reactor. In another embodiment, the HCC-240fa and HF are vaporized in the reactor.

The HF and HCC-240fa feeds are then adjusted to the desired mole ratio. The HF to HCC-240fa mole ratio preferably ranges from about 3:1 to about 100:1; more preferably from about 4:1 to about 50:1 and most preferably from about 5:1 to about 20:1.

The fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr to about 760 torr.

During the fluorination reaction, HCC-240fa and HF are reacted in a vapor phase with the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 8 hours to about 3 days, depending on the size of the reactor.

HFC-245fa may be recovered from the fluorination reaction product mixture comprised of unreacted starting materials, by-products including HCl, HCFC-1233 and a small amount of 1,3,3,3-tetrafluoropropene (HFC-1234) by any means known in the art, such as by extraction and preferably distillation. For example, the distillation may be preferably conducted in a standard distillation column at a pressure which is less than about 300 psig, preferably less than about 150 psig and most preferably less than 100 psig. The pressure of the distillation column inherently determines the distillation operating temperature. HCl may be recovered by operating the distillation column at from about −40° C. to about 25° C., preferably from about −40° C. to about −20° C. HCFC-1233 and HFC-1234 may be recovered by operating the distillation column at from about −10° C. to about 60° C. Single or multiple distillation columns may be used. The distillate portion includes substantially all the HCl, HCFC-1234, HCFC-1233/HFC-245fa azeotrope produced in the reaction and the bottoms portion includes the balance of HFC-245fa, HF and other impurities. In the preferred embodiment, the HCl is removed from the fluorination reaction products. More preferably, the HCl is removed prior to the recovery of HFC-245fa from the fluorination reaction mixture.

In the preferred embodiment, any HF present may also be recovered and recycled back for subsequent fluorination reactions. Preferably 1-chloro-3,3,3-trifluoropropene and 1,3,3,3-tetrafluoropropene are also recycled back to the vapor phase reactor to react with HF in subsequent fluorination runs or alternatively they are recycled back to a separate liquid phase reactor and reacted with HF. The liquid phase reaction is run at a preferred temperature ranging from about 25° C. to about 200° C.; more preferably from about 50° C. to about 150° C. and most preferably from about 70° C. to about 120° C. The liquid phase reactor pressure is preferably maintained at from about 50 psig to about 300 psig; more preferably from about 75 psig to about 200 psig and most preferably from about 100 psig to about 175 psig.

The liquid phase reactor contains a liquid phase fluorination catalyst. Such liquid phase fluorination catalysts non-exclusively include transition metal halides, Group IVb metal halides and Group Vb metal halides and mixtures thereof.

Such non-exclusively include $SbCl_5$, $SbCl_3$, $TaCl_5$, $SnCl_4$, $NbCl_5$, $TiCl_4$, $MoCl_5$ and mixtures thereof. The reactant is allowed to contact the liquid phase fluorination catalyst in a batch or continuous mode. Reaction time is sufficient to convert the reactants to HFC-245fa. Typically, the liquid phase reaction may be conducted at a catalyst contact time of from about 1 second to about 1 hour when conducted in a continuous mode and from about 1 hour to above 5 hours when conducted in a batch mode. The process herein described achieves a conversion of HCC-240 at a conversion rate of at least 99%. Liquid phase reaction conditions are well known in the art as described, for example, in U.S. Pat. No. 5,395,987 which is incorporated herein by reference.

In another embodiment of the invention, the above processes may be conducted by substituting one or more of 1,1-dichloro-3,3,3-trifluoropropane (HFC-243fa), 1-chloro-1,3,3,3,-tetrafluoropropane (HFC-244fa) and 1,1,3-trichloro-3,3-difluoropropane (HFC-242fa) for the 1,1,1,3,3-pentachloropropane (HCC-240fa) as the starting material for the fluorination reactions. Each of these is an intermediate in the fluorination of 1,1,1,3,3-pentachloropropane to 1,1,1,3,3-pentafluoropropane and 1-chloro-3,3,3-trifluoropropene. Therefore, instead of conducting the fluorination reactions with HCC-240fa and form HFC-243fa, HFC-244fa and/or HFC-242fa as in situ intermediates, one may directly use one or more of HFC-243fa, HFC-244fa and/or HFC-242fa as the starting material.

The preparation of these materials is known in the art or they may be prepared by a separate fluorination of HCC-240fa. The fluorination and separation reactions of this invention for the production of HFC-245fa and HCFC-1233 generally follow the same conditions given above when HFC-243fa, HFC-244fa and/or HFC-242fa are used instead of HCC-240fa. Any differences may be easily determined by those skilled in the art.

The invention illustratively disclosed herein suitably may be practiced in the absence of any components or steps which are not specifically disclosed herein. The following non-limiting examples serve to illustrate the invention.

EXAMPLES 1-4

About 132 g (about 1.33 g/cc bulk density) of a chromium (III) oxide catalyst, was charged to a reactor of 1" diameter Monel pipe. The catalyst was dried and pretreated with HF before use.

The reactor was preheated to the reaction temperature while anhydrous HF was fed to the reactor. An organic feed (HCC-240) was started when the reactor reached the desired temperature and pressure. The HF and organic feeds were then adjusted to the desired rates. The effluent product stream was analyzed by using an on-line Perkin Elmer model 8500 gas chromatograph having a column packed with 5% Fluoricol (GC).

Table 1 shows the reaction conditions, conversions and selectivities of the products. 1-Chloro-3,3,3-trifluoropropene appears to be the predominant product, which is a precursor of 1,1,1,3,3-pentafluoropropane (HFC-245fa). 1,3,3,3-tetrafluoropropenes are decomposition products of HFC-245fa. Recycle of 1-chloro-3,3,3-trifluoropropene and/or 1,3,3,3-tetrafluoropropene back to the reactor can make additional HFC-245fa. Alternatively, a subsequent liquid phase reactor can be used to convert these fluoro-olefins to HFC-245fa in yields of about 90% or more.

TABLE 1

| Example: | 1 | 2 | 3 | 4 |
| --- | --- | --- | --- | --- |
| Pressure (atm): | 1 | 1 | 1 | 1 |
| Temp (°C.): | 300 | 325 | 350 | 270 |
| Catalyst Life (hr): | 6 | 17 | 24 | 30 |
| HF Feed Rate (g/hr): | 105 | 96 | 108 | 74 |
| HCC-240 Feed Rate (g/hr): | 39 | 40 | 47 | 41 |
| Contact Time (sec): | 2.5 | 2.7 | 2.2 | 3.6 |
| HF/HCC-240 Mole Ratio: | 29 | 24 | 25 | 20 |
| Conversion (HCC-240%): | >99 | >99 | >99 | >99 |
| Selectivities (area %): | | | | |
| 1,3,3,3-tetrafluoropropene | | | | |
| -trans isomer | 4.0 | 4.9 | 6.5 | 1.6 |
| -cis isomer | 1.7 | 3.2 | 0.9 | 0.4 |
| 1,1,1,3,3-pentafluoropropane | 2.1 | 2.1 | 1.8 | 1.8 |
| 1-chloro-3,3,3-trifluoropropene | | | | |
| - trans isomer | 77 | 74 | 76 | 82 |
| - cis isomer | 14 | 13 | 13 | 13 |
| Dichlorotrifluoro-propane | 0 | 0 | 0 | 0.22 |
| Trichlorodifluoro-propane | 0 | 0 | 0 | 0.15 |

What is claimed is:

1. A process for the preparation of 1,1,1,3,3-pentafluoropropane comprising the steps of:

(a) conducting a fluorination reaction by reacting 1,1,1,3,3-pentachloropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene;

(b) separating 1,1,1,3,3-pentafluoropropane from said reaction product; and (c) subsequently recycling the 1-chloro-3,3,3-trifluoropropene and/or 1,3,3,3-tetrafluoropropene to a liquid phase reactor for reaction with HF to thereby produce additional 1,1,1,3,3 -pentafluoropropane.

2. The process of claim 1 wherein the liquid phase reaction is conducted with a fluorination catalyst selected from the group consisting of transition metal halides, Group IVb metal halides, Group Vb metal halides and mixtures thereof.

3. The process of claim 1 wherein the liquid phase reaction is conducted with a fluorination catalyst selected from the group consisting of $SbCl_5$, $SbCl_3$, $TaCl_5$, $SnCl_4$, $NbCl_5$, $TiCl_4$, $MoCl_5$ and mixtures thereof.

4. A process for the preparation of 1,1,1,3,3-pentafluoropropane comprising the steps of:

(a) conducting a fluorination reaction by reacting 1,1,1,3,3-pentachloropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene; and (b) separating 1,1,1,3,3-pentafluoropropane from said reaction product wherein said fluorination reaction is conducted with a fluorination catalyst selected from the group consisting of, chromium, aluminum, cobalt, manganese, nickel and iron oxides, hydroxides, halides, oxyhalides and inorganic salts thereof.

5. The process of claim 4 further comprising subsequently removing said HCl from said reaction product.

6. The process of claim 4 further comprising additionally removing HCl from said reaction product before said separation.

7. The process of claim 4 further comprising subsequently recovering any unreacted HF present after said separation and recycling it back for said reaction with 1,1,3,3,3-pentachloropropane.

8. The process of claim 4 wherein said 1,1,1,3,3-pentachloropropane is pre-vaporized.

9. The process of claim 4 wherein said HF is pre-vaporized.

10. The process of claim 4 wherein said 1,1,1,3,3-pentachloropropane and said HF are pre-vaporized.

11. The process of claim 4 wherein the 1,1,1,3,3-pentachloropropane and HF are vaporized in the reactor.

12. The process of claim 4 wherein said fluorination reaction is conducted at a temperature of from about 80° C. to about 400° C.

13. The process of claim 4 wherein said fluorination reaction is conducted at atmospheric pressure or under a vacuum.

14. The process of claim 4 wherein the fluorination catalyst is a chromium catalyst selected from the group consisting of, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$.

15. The process of claim 4 further comprising subsequently recycling the 1-chloro-3,3,3-trifluoropropene and/or 1,3,3,3-tetrafluoropropene and reacting the 1-chloro-3,3,3-trifluoropropene and/or 1,3,3,3-tetrafluoropropene with HF.

16. The process of claim 4 wherein said fluorination catalyst is chromium (III) oxide.

17. The process of claim 4 wherein said separation is conducted by distillation.

18. The process of claim 17 wherein the distillation is conducted at a pressure of from less than about 300 psig.

19. The process of claim 4 wherein the fluorination catalyst contact time is from about 1 second to about 120 seconds.

20. The process of claim 4 wherein the mole ratio of HF to 1,1,1,3,3-pentachloropropane ranges from about 3:1 to about 100:1.

21. The process of claim 4 wherein the conversion of 1,1,1,3,3-pentachloropropane is at least about 99%.

22. A process for the preparation of 1-chloro-3,3,3-trifluoropropene which comprises:
  (a) conducting a fluorination reaction by reacting 1,1,1,3,3-pentachloropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and
  (b) separating 1-chloro-3,3,3-trifluoropropene from said reaction product.

23. A process for the preparation of 1,1,1,3,3-pentafluoropropane which comprises:
  (a) conducting a fluorination reaction by reacting one or more components comprised of 1,1-dichloro-3,3,3-trifluoropropane, 1-chloro-1,3,3,3,-tetrafluoropropane or 1,1,3-trichloro-3,3-difluoropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and
  (b) separating 1,1,1,3,3-pentafluoropropane from said reaction product wherein said fluorination reaction is conducted with a fluorination catalyst selected from the group consisting of, chromium, aluminum, cobalt, manganese, nickel and iron oxides, hydroxides, halides, oxyhalides and inorganic salts thereof.

24. A process for the preparation of 1-chloro-3,3,3-trifluoropropene which comprises:
  (a) conducting a fluorination reaction by reacting one or more components comprised of 1,1-dichloro-3,3,3-trifluoropropane, 1-chloro-1,3,3,3,-tetrafluoropropane or 1,1,3-trichloro-3,3-difluoropropane with hydrogen fluoride in a reactor in the vapor phase and in the presence of a fluorination catalyst, thereby forming a reaction product comprising HCl, 1,1,1,3,3-pentafluoropropane, 1-chloro-3,3,3-trifluoropropene and 1,3,3,3-tetrafluoropropene, and
  (b) separating 1-chloro-3,3,3-trifluoropropene from said reaction product.

* * * * *

UNITED STATES PATENT AND TRADEMARK OFFICE
CERTIFICATE OF CORRECTION

PATENT NO : 5,710,352
DATED : January 20, 1998
INVENTOR(S) : Tung

It is certified that error appears in the above-identified patent and that said Letters Patent is hereby corrected as shown below:

Column 1, line 45, replace "IP" with -- JP --.

Claim 3, line 4, "TICL$_4$" should read -- TiCl$_4$ --.

Signed and Sealed this

Twentieth Day of March, 2001

*Attest:*

NICHOLAS P. GODICI

*Attesting Officer*     *Acting Director of the United States Patent and Trademark Office*